United States Patent
Irani et al.

(10) Patent No.: US 9,212,549 B2
(45) Date of Patent: Dec. 15, 2015

(54) REGULATION-COMPLIANT HOLDING DEVICE FOR STORING OR TRANSPORTING A NON-COMPLIANT CONTAINER

(75) Inventors: Cyrus A. Irani, Houston, TX (US); Scott L. Miller, Carrollton, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 713 days.

(21) Appl. No.: 13/114,169

(22) Filed: May 24, 2011

(65) Prior Publication Data
US 2012/0297903 A1   Nov. 29, 2012

(51) Int. Cl.
*E21B 49/08* (2006.01)
*G01N 1/02* (2006.01)
*G01N 1/00* (2006.01)

(52) U.S. Cl.
CPC ........ *E21B 49/08* (2013.01); *G01N 1/00* (2013.01); *G01N 1/02* (2013.01); *G01N 2001/005* (2013.01)

(58) Field of Classification Search
CPC .................................. G01N 1/02; E21B 49/08
USPC ....................................................... 73/864.91
See application file for complete search history.

(56) References Cited

U.S. PATENT DOCUMENTS

| | | | | |
|---|---|---|---|---|
| 4,880,119 A * | 11/1989 | Simon | | 206/584 |
| 6,074,610 A * | 6/2000 | Huang et al. | | 422/550 |
| 7,062,958 B2 * | 6/2006 | Diakonov et al. | | 73/152.23 |
| 2008/0066534 A1 * | 3/2008 | Reid et al. | | 73/152.11 |
| 2009/0255672 A1 * | 10/2009 | Simpson et al. | | 166/264 |
| 2010/0229661 A1 * | 9/2010 | Coleman et al. | | 73/864.63 |

OTHER PUBLICATIONS

American Petroleum Institute, "Recommended Practices for Core Analysis", second edition, Feb. 1998.*

* cited by examiner

*Primary Examiner* — Paul West
(74) *Attorney, Agent, or Firm* — McGuireWoods LLP

(57) ABSTRACT

According to an embodiment, a method of storing or transporting a sample comprises: inserting a sample container into a holding device, wherein the sample container contains the sample, wherein the sample container does not meet United States transportation regulations, wherein the holding device meets or exceeds United States transportation regulations, and wherein the holding device comprises a chamber and an opening; and storing or transporting the holding device. According to another embodiment, a holding device for containing a container comprises: a chamber; and an opening, wherein the holding device meets or exceeds United States transportation regulations, wherein the container contains a sample, and wherein United States regulations require the sample to be stored or transported according to the United States transportation regulations.

19 Claims, 2 Drawing Sheets

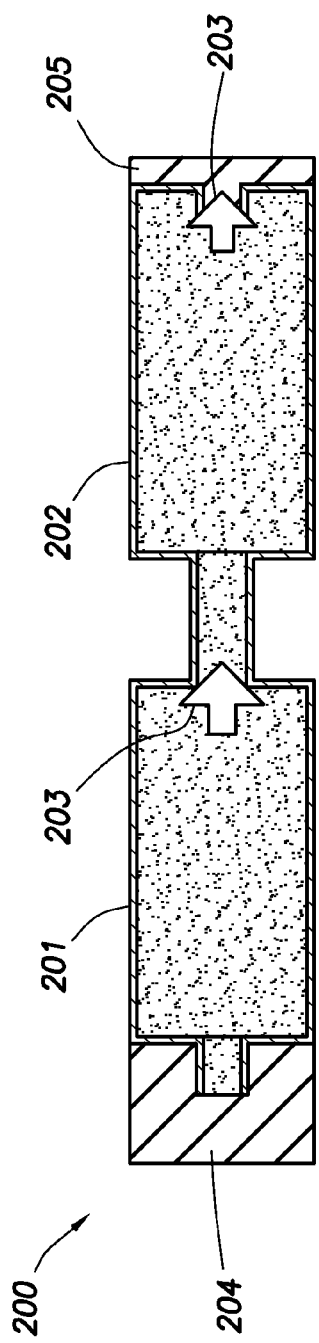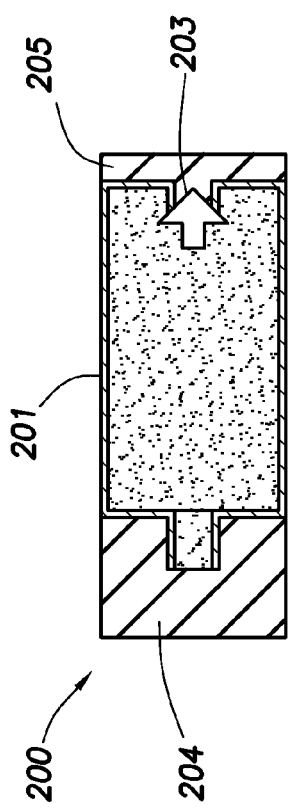

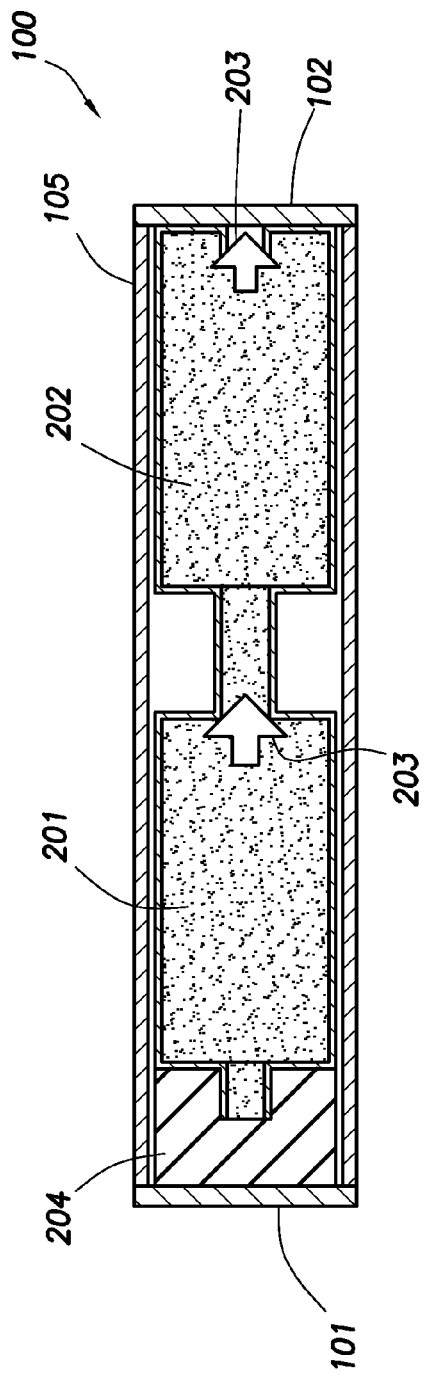
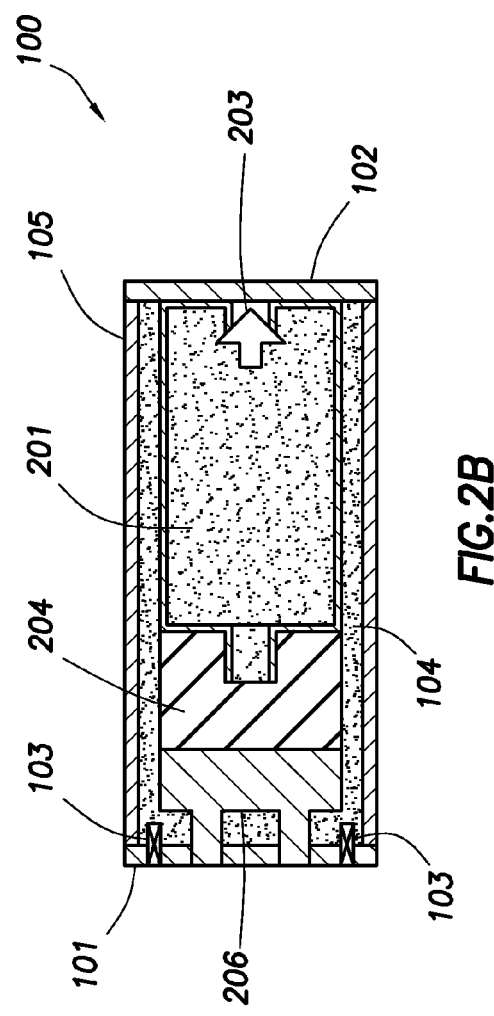

REGULATION-COMPLIANT HOLDING DEVICE FOR STORING OR TRANSPORTING A NON-COMPLIANT CONTAINER

TECHNICAL FIELD

A method of storing and/or transporting a container is provided. A holding device for containing a container is also provided. According to an embodiment, the container does not meet United States transportation regulations; whereas the holding device meets or exceeds the United States transportation regulations. According to another embodiment, the container contains a subterranean formation fluid sample.

SUMMARY

According to an embodiment, a method of storing or transporting a sample comprises: inserting a sample container into a holding device, wherein the sample container contains the sample, wherein the sample container does not meet United States transportation regulations, wherein the holding device meets or exceeds United States transportation regulations, and wherein the holding device comprises a chamber and an opening; and storing or transporting the holding device.

According to another embodiment, a holding device for containing a container comprises: a chamber; and an opening, wherein the holding device meets or exceeds United States transportation regulations, wherein the container contains a sample, and wherein United States transportation regulations require the sample to be stored or transported according to the United States transportation regulations.

BRIEF DESCRIPTION OF THE FIGURES

The features and advantages of certain embodiments will be more readily appreciated when considered in conjunction with the accompanying figures. The figures are not to be construed as limiting any of the preferred embodiments.

FIG. 1A is a diagram of a sample container including a sample receptacle.

FIG. 1B is a diagram of the sample container further including a pressurization compartment.

FIGS. 2A and 2B are diagrams according to certain embodiments of a holding device including a chamber for containing the sample container.

DETAILED DESCRIPTION

As used herein, the words "comprise," "have," "include," and all grammatical variations thereof are each intended to have an open, non-limiting meaning that does not exclude additional elements or steps.

It should be understood that, as used herein, "first," "second," "third," etc., are arbitrarily assigned and are merely intended to differentiate between two or more valves, seals, etc., as the case may be, and does not indicate any sequence. Furthermore, it is to be understood that the mere use of the term "first" does not require that there be any "second," and the mere use of the term "second" does not require that there be any "third," etc.

As used herein, a "fluid" is a substance having a continuous phase that tends to flow and to conform to the outline of its container when the substance is tested at a temperature of 71° F. (22° C.) and a pressure of one atmosphere "atm" (0.1 megapascals "MPa"). A fluid can be a liquid or gas. A fluid can have only one phase or more than one phase. In the oil and gas industry, a fluid having only one phase is commonly referred to as a single-phase fluid and a fluid having more than one phase is commonly referred to as a multi-phase fluid. If a single-phase fluid is subjected to sufficient changes in pressure or temperature, then the fluid system can become unstable. As used herein, the term "unstable" means that a single-phase fluid undergoes a phase separation, causing the single-phase fluid to become a multi-phase fluid.

Many countries, such as the United States ("U.S."), have governmental agencies that regulate the storage and/or transportation of certain substances. An example of an agency in the U.S. that regulates storage and/or transportation of the substances is the Department of Transportation ("DOT"). Examples of classes of substances that are currently regulated by the DOT can include, but are not limited to: explosives; flammable materials; corrosive materials; certain gases; radioactive materials; and hazardous materials, such as infectious materials and pressurized material. Each class can include several unique substances.

It is common for a governmental agency to impose requirements for the containers that regulated substances are to be stored or transported in. Container requirement examples include, but are not limited to: the container must be labeled in a manner to clearly identify the class of the substance located within the container; the container must be made of a specific type of material depending on which class of substance is to be placed in the container; the container material may have to be a certain thickness depending on the substance class; and in some instances, the container may not be filled with more than a certain volume of the substance. One class of substances may have its own unique container requirements; whereas, another class of substances may have different container requirements. In order to ensure compliance with governmental regulations, the substance should be identified as belonging to a regulated class of substances. Then, the regulations for that class of substances can be evaluated to determine the appropriate specifications for the container the substance is to be placed in.

In the oil and gas industry it is often desirable to take a sample of a subterranean formation fluid, also referred to as a reservoir fluid. The reservoir fluid is generally a single-phase fluid. A formation fluid belongs to a class of substances regulated in the U.S. by the DOT. There are a variety of instruments that can be used to collect a sample of formation fluids. One such instrument is the ARMADA® sampling system, marketed by Halliburton Energy Services, Inc. In order to collect a sample, the sampling system is placed into a wellbore at a desired location. The sampling system functions to collect a sample of the formation fluids (the desirable fluid) at that location. The sampling system is then returned to the surface where the sample can be retrieved from the system. In some instances, fluids other than the desired fluid will be collected along with the desired fluid. For example, if oil is the desired reservoir fluid to be collected, water (the undesired fluid) may also be collected along with the oil. It is to be understood that any reference herein to "the sample" is meant to apply to the desired fluid. For example, if an embodiment specifies the stability of the sample, then such embodiment is meant to pertain only to the stability of the desired fluid and is not meant to apply to the stability of any undesired fluid that may be collected along with the desired fluid.

Reservoirs are typically located in the range of a few hundred feet (shallow reservoirs) to a few tens of thousands of feet (ultra-deep reservoirs). In order to produce oil or gas, a wellbore is drilled into a reservoir or adjacent to a reservoir. A wellbore can extend several hundreds of feet below the earth's surface or several hundreds of feet below the surface of a body of water in off-shore drilling. There can be a difference in temperature at different depths of the formation. For example, as the depth of a wellbore increases below the earth's surface, the temperature generally increases. Moreover, as the depth of a wellbore increases below the surface of a body of water, the temperature generally decreases. A collected formation sample can be subjected to changes in temperature as the sample is carried through the hundreds to thousands of feet to the surface; thus, causing the desired fluid to become unstable.

To avoid destabilizing the fluid, some sampling systems include a separate compartment whereby the sample can be pressurized. One way to pressurize a sample is to inject a gas, such as nitrogen, into a pressurization compartment. The compartment can be pressurized to a desired pressure with the injected gas based on the anticipated temperature change. The increased pressure helps maintain the sample as a stable fluid.

It is common to collect a sample of a substance in a container. In some instances the container may not meet governmental regulations and can be called a non-compliant container. Because these containers are non-compliant, the sample must be removed from the non-compliant container and transferred into a compliant container. However, it may be undesirable to transfer the sample to a new container. For example, transferring the sample may expose people to possible injury or health risks, and compromise the sample itself due to a failed transfer process. It is also inefficient and less convenient to transfer a sample into a compliant container.

Thus, there is a need for a holding device that meets or exceeds U.S. transportation regulations whereby a non-compliant container can be inserted into the compliant holding device for storage and/or transportation.

A novel holding device that meets or exceeds U.S. regulations comprising a chamber and an opening can be used for storing or transporting a sample container, wherein the sample container does not meet the U.S. regulations.

According to an embodiment, a holding device for containing a container comprises: a chamber; and an opening, wherein the holding device meets or exceeds United States transportation regulations, wherein the container contains a sample, and wherein United States transportation regulations require the sample to be stored or transported according to the United States transportation regulations.

According to another embodiment, a method of storing or transporting a sample container comprises: inserting a sample container into a holding device, wherein the sample container contains the sample, wherein the sample container does not meet United States transportation regulations, wherein the holding device meets or exceeds United States transportation regulations, and wherein the holding device comprises a chamber and an opening; and storing or transporting the holding device.

Any discussion of the embodiments regarding the holding device, the sample container, or any components thereof, is intended to apply to the apparatus embodiments and the method embodiments. Any discussion of a particular component of the holding device or the sample container (e.g., a valve) is meant to include the singular form of the component and also the plural form of the component, without the need to continually refer to the component in both the singular and plural form throughout. For example, if a discussion involves "the valve 203," it is to be understood that the discussion pertains to one valve (singular) and two or more valves (plural).

Turning to the Figures. FIGS. 1A and 1B are diagrams of a sample container 200. According to an embodiment, the sample container 200 does not meet United States transportation regulations. As can be seen in FIG. 1B, the sample container 200 comprises a sample receptacle 201. The sample receptacle 201 will have two ends; a first end and a second end. The sample receptacle 201 can include a first opening. The sample receptacle 201 can also include a second opening. The openings can be located at the first and second ends. The sample receptacle 201 can contain a sample. The sample can be introduced into the sample receptacle 201 via the first and/or second openings. The sample can be a substance, such as a solid, liquid, gas, or combinations thereof. According to an embodiment, the sample is a substance that is regulated by a U.S. agency. According to another embodiment, the sample is a substance that is regulated by the U.S. DOT. According to another embodiment, the sample is a subterranean formation fluid. According to another embodiment, the sample container 200 is part of the ARMADA® sampling system, marketed by Halliburton Energy Services, Inc.

The sample container 200 can further comprise a valve 203. The valve 203 can be a one-way valve. As used herein, the term "one-way valve" means a device that allows a fluid to enter a space within an enclosed area in one direction, but does not independently allow the fluid to exit the space in a reverse direction. Of course, a one-way valve may have a release mechanism whereby a person can activate the mechanism thereby causing at least some of the fluid within the sample retaining space to flow out of the enclosed area. However, the one-way valve should be designed such that any fluid that enters the space will not freely flow back out of that space without external intervention. The valve 203 can be positioned in an opening of the sample receptacle 201. The valve 203 can be located at the first end or the second end of the sample receptacle 201, or one valve 203 can be located at the first end and another valve 203 can be located at the second end. A sample can be introduced into the sample receptacle 201 via the valve 203 positioned in the opening of the sample receptacle 201. In this manner, the sample can be contained inside the sample receptacle 201 until a time when it is desirable to remove the sample from the sample receptacle 201.

As can be seen in FIG. 1A, the sample container 200 can further include a pressurization compartment 202. The pressurization compartment 202 will have two ends; a first end and a second end. The pressurization compartment 202 can include one or more openings. The opening(s) are preferably located at the end(s) of the pressurization compartment 202. According to an embodiment, the pressurization compartment 202 is detachably connected to the sample receptacle 201. The first end of the pressurization compartment 202 can be detachably connected to the first end of the sample receptacle 201, thus forming a center of the sample container 200. The sample container 200 can now include the sample receptacle 201 having an outermost end (the second end) and the pressurization compartment 202 having an outermost end (the second end). As used herein, the term "outermost" means the location(s) that is the farthest away from the center of an object.

According to an embodiment, the pressurization compartment 202 is capable of receiving a pressurization medium, such as a gas. The pressurization compartment 202 can also include a valve 203. The valve 203 can be located in an opening of the pressurization compartment 202. The valve 203 can be located at the first and/or second end of the pressurization compartment 202. The valve 203 can be a one-way valve. The pressurization medium can be introduced into the pressurization compartment 202 via the valve 203 located in the opening. The pressurization medium can be introduced such that a desired pressure is maintained in the pressurization compartment 202. For example, a sufficient volume of the pressurization medium can be introduced to maintain the desired pressure in the pressurization compartment 202. There may be a variety of reasons for including a pressurization compartment 202. One reason may be when the sample is a single-phase fluid, the sample can be subjected to temperature changes, and it is desirable to maintain the sample as a stable fluid. The pressurization compartment 202 can be connected to the sample receptacle 201 in a manner such that a pressure, for example gas pressure, from the pressurization compartment 202 maintains the sample located within the sample receptacle 201 as a stable fluid. According to another embodiment, the desired pressure in the pressurization compartment 202 is at least a sufficient pressure to maintain the sample as a stable fluid.

The sample receptacle 201 can be detachably connected at the first end to the first end of the pressurization compartment 202. When the sample container 200 does not include the pressurization compartment 202, a sample can be introduced into the sample receptacle 201 via the first end comprising an opening and/or the second end comprising an opening of the sample receptacle 201. The sample can be introduced into the first end of the sample receptacle 201 via the valve 203 or into the second end of the receptacle 201 via a valve 203 (not shown). When the sample container 200 includes the pressurization compartment 202, a sample can be introduced into the sample receptacle 201 via the second end of the sample receptacle 201 via a valve 203 (not shown).

The sample container 200 can further comprise a first seal 204. The first seal 204 can be positioned adjacent to the sample receptacle 201. As depicted in FIG. 1B, the first seal 204 can be positioned at the second end of the sample receptacle 201 opposite of the valve 203. The second end of the sample receptacle 201 can include an opening. According to an embodiment, the seal is designed such that once in place, a sample located within the sample receptacle 201 is not capable of independently exiting the sample receptacle 201. By including the first seal 204 at this second end, the sample can be contained within the sample receptacle 201. The sample receptacle 201 can further include a second seal 205. As can be seen in FIG. 1B, the second seal 205 can be positioned at the first end of the sample receptacle 201. According to an embodiment, the second seal 205 is positioned at the first end of the sample receptacle 201 adjacent to the valve 203. If the sample receptacle 201 includes both a first and second seal 204/205, then preferably, the second seal 205 is positioned at the end of the sample receptacle 201 opposite the end of the sample receptacle 201 that includes the first seal 204. By including the first and second seals 204/205, any sample located within the sample receptacle 201 can be contained. As can be seen in FIG. 1A, the second seal 205 can be positioned adjacent to the pressurization compartment 202. According to this embodiment, the second seal 205 can be positioned at the second end of the pressurization compartment 202 adjacent to the valve 203. When the sample container 200 includes both, the sample receptacle 201 and the pressurization compartment 202, the first seal 204 can be used to seal the outermost end of the sample receptacle 201 and the second seal 205 can be used to seal the outermost end of the pressurization compartment 202. Of course, according to this embodiment, the first end of the sample receptacle 201 will be detachably connected to the first end of the pressurization compartment 202 to form a center of the sample container 200.

The seals 204/205 can be permanently attached, removably attached, and combinations thereof to the sample container 200. By way of example, the first seal 204 can be removably attached to the sample receptacle 201 and the second seal 205 can be removably attached to the pressurization compartment 202. In this manner, once a sample has been collected and is located inside the sample receptacle 201, the sample can be contained within the sample receptacle 201 by attaching the first seal 204 to the outermost end (the second end) of the sample receptacle 201 and by attaching the second seal 205 to the outermost end (the second end) of the pressurization compartment 202. By way of another example, the first seal 204 can be permanently attached to the second end of the sample receptacle 201 and the second seal 205 can be removably attached to the first end of the sample receptacle 201. In this manner, once a sample has been collected and is located inside the sample receptacle 201, the sample can be contained within the sample receptacle 201 via the permanently attached first seal 204 and by attaching the second seal 205 to the first end of the sample receptacle 201. By way of another example, the first seal 204 and the second seal 205 can be removably attached to the sample receptacle 201. In this manner, once a sample has been collected and is located inside the sample receptacle 201, the first seal 204 can be attached to the outermost end (the second end) of the sample receptacle 201, the sample receptacle 201 can be disconnected from the pressurization compartment 202, and the second seal 205 can then be attached to the first end of the sample receptacle 201.

FIGS. 2A and 2B are diagrams of the holding device 100 according to certain embodiments. According to an embodiment, the holding device 100 meets or exceeds United States ("U.S.") transportation regulations. In another embodiment, the sample container 200 does not meet U.S. transportation regulations, but the holding device 100 meets or exceeds U.S. transportation regulations.

The holding device 100 comprises a chamber 105 and an opening. In an embodiment, the holding device 100 is capable of completely surrounding the sample container 200. The shape of the chamber 105 can be selected such that the holding device 100 is capable of completely surrounding the sample container 200. The sample container 200 may be a variety of shapes, as such the chamber 105 may also be a variety of shapes. The shape of the chamber 105 and the shape of the sample container 200 can be the same, similar, or different. Examples of possible shapes of the sample container 200 and the chamber 105 include, but are not limited to, circular, rounded, orbicular, elliptical, cylinoidal, cylindrical, polygonal, frustrum, or conical. In an embodiment, the size of the chamber 105 is selected such that the holding device is capable of completely surrounding the sample container 200.

The methods include the step of inserting the sample container 200 into the holding device 100. The sample container 200 can fit in a variety of ways inside the holding device 100. For example, the sample container 200 can fit closely inside the holding device 100. For a close fit, the shape and size of the chamber 105 can be selected such that the sample container 200 has limited vertical or lateral movement inside the holding device 100. By way of another example, the sample container 200 can fit loosely inside the holding device 100. For a loose fit, the shape and size of the chamber 105 can be selected such that an annulus 104 exists between the sample container 200 and the holding device 100. As used herein, the term "annulus" means the space between two objects, one inside the other. For example, an annulus 104 can exist between the inside of the chamber 105 and the outside of the sample container 200. As used herein, the term "inside" means the inner perimeter or circumference of an object. As used herein, the term "outside" means the outer perimeter or circumference of an object. By way of another example, an annulus 104 can exist between one or more of the outermost ends of the sample container 200 and the ends of the holding device 100.

The holding device 100 also includes two ends. In an embodiment, at least one of the ends is the opening. Preferably, the sample container 200 is capable of being placed inside the holding device 100 via the opening. The holding device 100 can further comprise a first end seal 101. The first end seal 101 can be permanently attached or removably attached to a first end of the chamber 105. The holding device 100 can also include a second end seal 102. The second end seal 102 can be permanently attached or removably attached to a second end of the chamber 105. If the first end seal 101 is permanently attached to the first end of the chamber 105, then preferably, the second end of the chamber 105 is the opening. Moreover, if the first end seal 101 is permanently attached to the first end of the chamber 105, then preferably, the second end seal 102 is removably attached to the second end of the chamber 105.

The first and/or second end seals 101/102 can include an opening. As can be seen in FIG. 2A, the sample container 200, comprising the sample receptacle 201 and the pressurization compartment 202, is positioned inside the holding device 100. As can be seen in FIG. 2B, the sample receptacle 201 can be detached from the pressurization compartment 202 and the sample container 200 can then be positioned inside the holding device 100. Although not shown in FIGS. 2A and 2B, the sample container 200 can include the second seal 205.

The holding device 100 can further include a holding device valve 103. In an embodiment, the holding device valve 103 is positioned adjacent to the end seal 101/102 within the opening. The holding device valve 103 can be a one-way valve. The holding device 100 can be connected to a pressurization delivery source. The delivery source can contain a pressurization medium and be equipped with a pump. The pressurization medium (shown in FIG. 2B as dots within the annulus 104) can be a gas, for example, nitrogen. The holding device 100 can be operatively connected to the delivery source such that the pressurization medium can be pumped into the holding device 100 via the opening and the holding device valve 103. In an embodiment, the holding device 100 is capable of being filled with the pressurization medium to a desired pressure. An example of when it may be useful to pressurize the holding device 100 is when the sample container 200 does not include the pressurization compartment 202. In this example, the sample is not pressurized and may not remain as a stable fluid if subjected to changes in temperature. As such, it may be desirable to pressurize the holding device 100. In an embodiment, the holding device 100 is pressurized to a desired pressure. The desired pressure can be a sufficient pressure to maintain the sample as a stable fluid.

As can be seen in FIG. 2A, the shape and size of the chamber 105 may be such that only a very small annulus 104 or no annulus 104 exists between the inside of the chamber 105 and the outside of the sample container 200. If it is desirable to pressurize the holding device 100, then the shape and size of the chamber 105 can be designed to provide an annulus 104. For example, the length of the chamber 105 may be increased to provide an annulus 104 between at least one end of the holding device 100 and at least one of the outermost ends of the sample container 200. As can be seen in FIG. 2B, the size of the perimeter or circumference of the chamber 105 may be increased to provide an annulus 104 between the inside of the chamber 105 and the outside of the sample container 200. The sample container 200 can also include a pressurization adapter 206. According to an embodiment, the pressurization adapter 206 is positioned at a location on the sample container 200 such that the pressurization adapter 206 helps to create an annulus 104 between the container and the holding device. For example, the pressurization adapter 206 can be positioned at the first end of the sample container 200 adjacent to the first seal 204. By way of another example, the pressurization adapter 206 can be positioned at the second end of the sample container 200. In the preceding example, the pressurization adapter 206 can be adjacent to a valve 203 or a second seal 205 (not shown in FIGS. 2A and 2B). The size of the chamber is preferably sufficient to accommodate the entire length of the sample container 200 including the pressurization adapter 206.

The pressurization adapter 206 can include at least one protrusion. The at least one protrusion can be used to help create an annulus 104 between the container 200 and the holding device 100. The first end seal 101 can contain at least one appropriately-sized opening to accommodate the at least one protrusion. In this manner, the at least one protrusion is capable of being inserted into the at least one opening such that a seal is created at that end of the holding device.

In an embodiment, a method of storing or transporting a substance comprises: inserting the sample container 200 into the holding device 100 and storing or transporting the holding device. The methods can further include the step of collecting a sample prior to the step of inserting. The sample can be collected in the sample receptacle 201. If the sample container 200 also includes a pressurization compartment 202, then the methods can also include the step of pressurizing the pressurization compartment 202 prior to the step of inserting. If the sample container 200 also includes a pressurization compartment 202, then the methods can also include the step of separating the sample receptacle 201 from the pressurization compartment 202 prior to the step of inserting. The methods can further include the step of pressurizing the holding device 100 after the step of inserting. The methods can further include the step of pressurizing the pressurization compartment 202 and/or the holding device 100 to a desired pressure. According to an embodiment, the desired pressure is a pressure sufficient to maintain the sample as a stable fluid.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is, therefore, evident that the particular illustrative embodiments disclosed above may be altered or modified and all such variations are considered within the scope and spirit of the present invention. While compositions and methods are described in terms of "comprising," "containing," or "including" various components or steps, the compositions and methods also can "consist essentially of" or "consist of" the various components and steps. Whenever a numerical range with a lower limit and an upper limit is disclosed, any number and any included range falling within the range is specifically disclosed. In particular, every range of values (of the form, "from about a to about b," or, equivalently, "from approximately a to b,") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent(s) or other documents that may be incorporated herein by reference, the definitions that are consistent with this specification should be adopted.

What is claimed is:

1. A method of storing or transporting a sample comprising:
   introducing a sample container into a subterranean formation,
   collecting the sample in the sample container, wherein the sample container is positioned within the subterranean formation during collection;
   inserting the sample container into a holding device,
      wherein the step of inserting is performed at the surface of a wellbore that penetrates the subterranean formation,
      wherein the holding device comprises a holding device valve, a chamber, and an opening; and
   storing or transporting the holding device, wherein the step of storing or transporting is performed after the step of inserting.

2. The method according to claim 1, wherein the sample container comprises a sample receptacle.

3. The method according to claim 2, wherein the sample container further includes a pressurization compartment, wherein the pressurization compartment is detachably connected to the sample receptacle.

4. The method according to claim 3, further comprising the step of separating the sample receptacle from the pressurization compartment prior to the step of inserting.

5. The method according to claim 3, further comprising the step of pressurizing the pressurization compartment prior to the step of inserting.

6. The method according to claim 5, wherein the pressurization compartment is pressurized to a desired pressure.

7. The method according to claim 1, wherein the sample container further comprises a valve.

8. The method according to claim 1, wherein the sample container further comprises a seal.

9. The method according to claim 8, wherein the seal is permanently attached or removably attached to the sample container.

10. The method according to claim 1, wherein the holding device is capable of completely surrounding the sample container.

11. The method according to claim 1, wherein the sample container fits closely inside the holding device.

12. The method according to claim 11, wherein the shape and size of the chamber is selected such that the sample container has limited vertical or lateral movement inside the holding device after insertion into the holding device.

13. The method according to claim 11, wherein the shape and size of the chamber is selected such that an annulus exists between the sample container and the holding device after insertion into the holding device.

14. The method according to claim 1, wherein the holding device further comprises an end seal.

15. The method according to claim 14, wherein the end seal is permanently attached or removably attached to an end of the chamber.

16. The method according to claim 1, further comprising the step of collecting the sample prior to the step of inserting.

17. The method according to claim 1, further comprising the step of pressurizing the holding device after the step of inserting.

18. The method according to claim 17, wherein the holding device is pressurized to a desired pressure.

19. The method according to claim 1, wherein the sample container fits loosely inside the holding device.

* * * * *